(12) United States Patent
Park et al.

(10) Patent No.: US 11,298,431 B2
(45) Date of Patent: Apr. 12, 2022

(54) METHOD FOR LABELING RADIOISOTOPE RADIOLABELING COMPOUND AND KIT COMPRISING THE SAME FOR LABELING RADIOISOTOPE

(71) Applicant: KOREA ATOMIC ENERGY RESEARCH INSTITUTE, Daejeon (KR)

(72) Inventors: Sang Hyun Park, Seoul (KR); Sajid Mushtaq, Jeongeup-si (KR); Dae Seong Choi, Jeonju-si (KR); Beom Su Jang, Daejeon (KR); Eui-Baek Byun, Daejeon (KR); Jongho Jeon, Jeongeup-si (KR); Dong-Eun Lee, Jeonju-si (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 16/512,517

(22) Filed: Jul. 16, 2019

(65) Prior Publication Data
US 2020/0023085 A1 Jan. 23, 2020

(30) Foreign Application Priority Data

Jul. 17, 2018 (KR) ............ 10-2018-0083020
May 8, 2019 (KR) ............ 10-2019-0053872

(51) Int. Cl.
| | | |
|---|---|---|
| *A61K 51/04* | (2006.01) | |
| *G01N 33/533* | (2006.01) | |
| *A61K 51/02* | (2006.01) | |
| *G01N 33/534* | (2006.01) | |
| *A61K 51/08* | (2006.01) | |
| *A61K 51/12* | (2006.01) | |
| *A61K 51/10* | (2006.01) | |

(52) U.S. Cl.
CPC ........ *A61K 51/0453* (2013.01); *A61K 51/025* (2013.01); *A61K 51/0446* (2013.01);
(Continued)

(58) Field of Classification Search
None
See application file for complete search history.

(56) References Cited

U.S. PATENT DOCUMENTS

2013/0034497 A1 2/2013 Schmitt-Willich et al.

FOREIGN PATENT DOCUMENTS

| KR | 10-2017-0031305 A | 3/2017 |
|---|---|---|
| KR | 10-1755295 B1 | 7/2017 |
| WO | 9732862 A1 | 9/1997 |
| WO | 2014145493 A1 | 9/2014 |

OTHER PUBLICATIONS

Mushtaq et al. Efficient and Site-Specific 125I-Radioiodination of Bioactive Molecules Using Oxidative Condensation Reaction. 2018 ACS Omega 3: 6903-6911. Epub Jun. 26, 2018. (Year: 2018).*

(Continued)

*Primary Examiner* — Jennifer Lamberski
(74) *Attorney, Agent, or Firm* — Mintz Levin Cohn Ferris Glovsky and Popeo, P.C.; Peter F. Corless; Joohee Lee

(57) ABSTRACT

The present disclosure relates to a method for labeling a radioisotope, a radiolabeling compound, a kit including the same, and a method for labeling a radioisotope, including: providing a diaminophenyl compound represented by Chemical Formula I below and including a biomolecule, a fluorescent dye or a nanoparticle compound bound thereto; and reacting the diaminophenyl compound and a radioisotope-labeled aldehyde compound represented by Chemical Formula II below at room temperature; and a related technology:

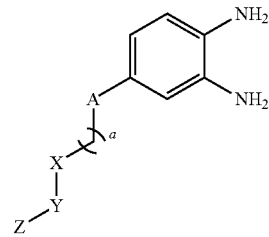

Chemical Formula I in Chemical Formula I,
A is $CH_2$ or O; a is 0 or an integer of 1 to 10; X is $CH_2$ or —CONH—; Y is $CH_2$ or

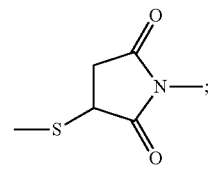

and Z is the biomolecule, the fluorescent dye or the nanoparticle compound,

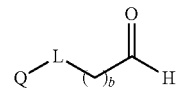

Chemical Formula II (Continued)

in Chemical Formula II, b is 0 or an integer of 1 to 10; and
L is CH$_2$ or —CONH—; and Q is

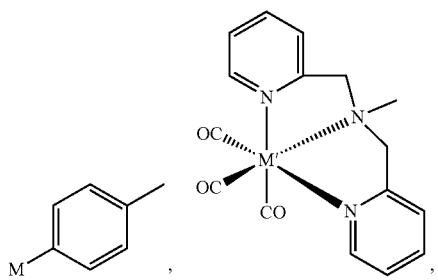

,

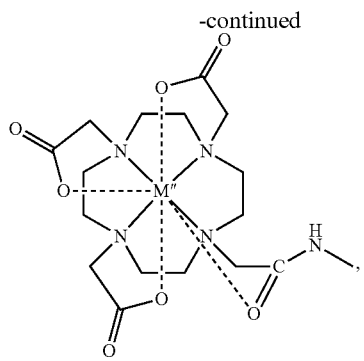

,

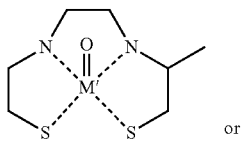 or

M, M' and M" in Q are radioisotopes.

16 Claims, 3 Drawing Sheets

Specification includes a Sequence Listing.

(52) U.S. Cl.
CPC ........ *A61K 51/0482* (2013.01); *A61K 51/081* (2013.01); *A61K 51/10* (2013.01); *A61K 51/1244* (2013.01); *G01N 33/533* (2013.01); *G01N 33/534* (2013.01)

(56) References Cited

OTHER PUBLICATIONS

Chunchi Lin, et al., 'Using Molecular Iodine in Direct Oxidative Condensation of Aldoses with Diamines: An Improved Synthesis of Aldo-benzimidazoles and Aldo-naphthimidazoles for Carbohydrate Analysis', J. Org. Chem. 2008, vol. 73, No. 10, pp. 3848-3853.

* cited by examiner

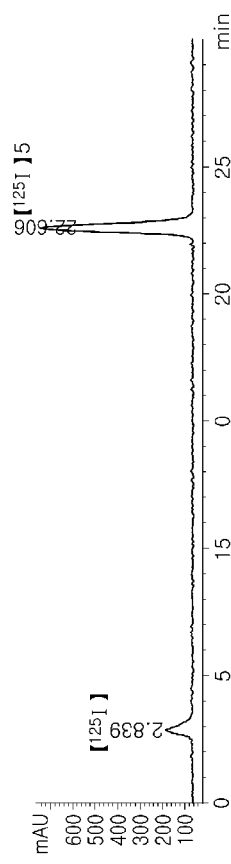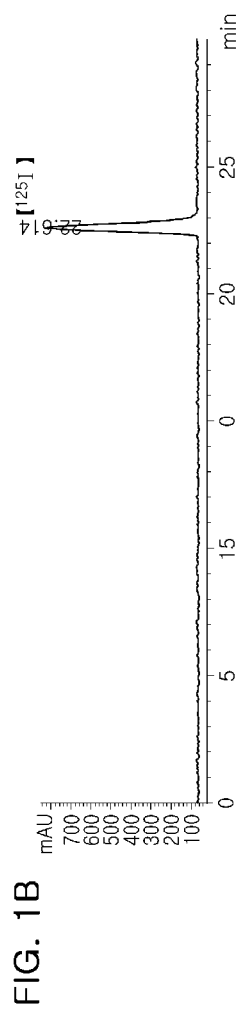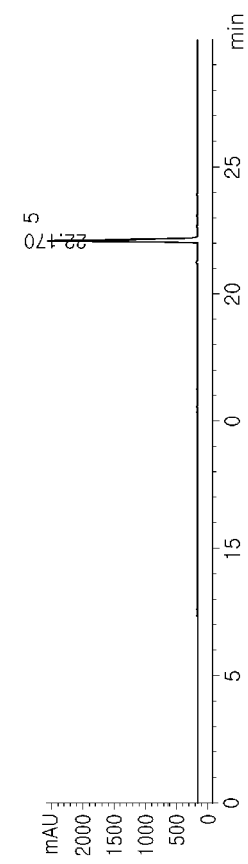
FIG. 1A
FIG. 1B
FIG. 1C

SEQUENCE LISTING

<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: CGNSNPKSC peptide

<400> SEQUENCE: 1

Cys Gly Asn Ser Asn Pro Lys Ser Cys
1               5

<210> SEQ ID NO 2
<211> LENGTH: 7
<212> TYPE: PRT
<213> ORGANISM: Artificial Sequence
<220> FEATURE:
<223> OTHER INFORMATION: VHSPNKK peptide

<400> SEQUENCE: 2

Val His Ser Pro Asn Lys Lys
1               5

<210> SEQ ID NO 3
<211> LENGTH: 10
<212> TYPE: PRT
<213> ORGANISM: Artificial Sequence
<220> FEATURE:
<223> OTHER INFORMATION: CTTHWGFTLC peptide

<400> SEQUENCE: 3

Cys Thr Thr His Trp Gly Phe Thr Leu Cys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: SGKGPRQITAL peptide

<400> SEQUENCE: 4

Ser Gly Lys Gly Pro Arg Gln Ile Thr Ala Leu
1               5                   10

<210> SEQ ID NO 5
<211> LENGTH: 5
<212> TYPE: PRT
<213> ORGANISM: Artificial Sequence
<220> FEATURE:
<223> OTHER INFORMATION: SGRSA peptide

<400> SEQUENCE: 5

Ser Gly Arg Ser Ala
1               5

```
<210> SEQ ID NO 6
<211> LENGTH: 7
<212> TYPE: PRT
<213> ORGANISM: Artificial Sequence
<220> FEATURE:
<223> OTHER INFORMATION: FSRYLWS peptide

<400> SEQUENCE: 6

Phe Ser Arg Tyr Leu Trp Ser
1               5
```

METHOD FOR LABELING RADIOISOTOPE RADIOLABELING COMPOUND AND KIT COMPRISING THE SAME FOR LABELING RADIOISOTOPE

CROSS-REFERENCE TO RELATED APPLICATION(S)

This application claims benefit of priority to Korean Patent Application No. 10-2018-0083020 filed on Jul. 17, 2018 and Korean Patent Application No. 10-2019-0053872 filed on May 8, 2019 in the Korean Intellectual Property Office, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 31, 2020, is named 049266-519001US_Sequence Listing.txt and is 1,498 bytes in size.

BACKGROUND

1. Field

The present disclosure relates to a method for labeling a radioisotope, and a radiolabeling compound and a kit including the same for labeling a radioisotope, and more particularly, to a technology using a method for labeling a radioisotope in which accumulation in the thyroid is remarkably reduced, a radiolabeling compound and a kit including the same for labeling a radioisotope, and the like, which may be applied in the field of medical diagnosis and treatment.

2. Description of Related Art

A radioisotope labeling technology for a biomolecule has been developed to use physiologically active substances such as peptides, proteins, and antibodies, and the like, for purposes of molecular imaging or disease diagnosis/treatment. In the related art, a method for binding a chelator to a physiologically active substance has mainly been used. This method is a method in which a separate chelator is chemically introduced into the physiologically active substance, and has a fundamental limitation to improve a low reaction rate or reaction conditions not suitable for the physiologically active substance, for example, a high temperature reaction, an acidic or basic reaction, a toxic reaction solvent, and the like, when binding to the chelator.

Typically, for the past few decades, radioactive iodine has been used for radioactive labeling of biomolecules for diagnostic and therapeutic purposes. Specifically, $^{124}$I is a radioactive iodine mainly used for positron emission tomography (PET), $^{123}$I and $^{125}$I are radioactive iodines used mainly for single photon emission computed tomography (SPECT), and $^{131}$I is a radioactive iodine used for the diagnosis and treatment of diseases such as thyroid cancer.

As described above, as radioactive iodine is widely used medically, various labeling methods for labeling radioactive iodine in biomolecules and small unit molecules have been developed. Thereamong, an electrophilic aromatic substitution reaction is a method capable of directly labeling a radioisotope, and shows high efficiency. However, most of the labeled compounds synthesized through the above labeling method are unstable in an animal body, and thus there are many cases that desired image results are not obtained, and a strong oxidant used for labeling exhibited a decrease in physiological activity of biomaterials. A method for indirect labeling synthesis of radioactive iodine capable of solving the above-described problems has been studied, and several prosthetic groups have been developed. However, the method for indirect labeling radioactive iodine, which has been developed to date, has problems in that there are many cases where a random labeling compound is generated due to lack of chemical selectivity for an active group, and an excessive amount of substrate is required for a high yield due to a slow reaction rate.

Thus, it is necessary to develop a novel method for labeling a radioactive iodine which is stable in living cells and animals and is capable of being employed as an imaging diagnostic and therapeutic substance in which accumulation in a living body such as thyroid, or the like, is reduced. Korean Patent Laid-Open Publication No. 2012-0101073 which is a related art regarding this method discloses iodine-labeled homoglutamic acid and glutamic acid derivatives, and discloses a technology relating to $^{125}$I-labeled homoglutamic acid and glutamic acid derivatives. However, the related art has a problem that uptake in blood may be insufficient.

Therefore, when there is provided a radiolabeling compound capable of labeling a radioisotope on a biomolecule, a fluorescent dye, or a nanoparticle compound, using the radiolabeling compound and the biomolecule, or the like, at a rapid reaction rate and a high radiochemical yield, and having a low degree of accumulation in thyroid, or the like, but improved uptake in blood, it is expected that the radiolabeling compound is capable of being usefully utilized for radioisotope labeling and medical diagnosis on the biomolecule, or the like.

SUMMARY

An aspect of the present disclosure may provide a method for labeling a radioisotope using an aldehyde-diamine condensation reaction.

An aspect of the present disclosure may also provide a radiolabeling compound for labeling a molecule having an amine moiety.

An aspect of the present disclosure may also provide a kit for labeling a radioisotope using an aldehyde-diamine condensation reaction.

An aspect of the present disclosure may also provide a radiolabeling compound for labeling a molecule having a thiol moiety.

An aspect of the present disclosure may also provide a radioisotope-labeled biomolecule, a radioisotope-labeled fluorescent dye or a radioisotope-labeled nanoparticle compound.

An aspect of the present disclosure may also provide a composition for medical diagnosis including the radioisotope-labeled biomolecule, the radioisotope-labeled fluorescent dye or the radioisotope-labeled nanoparticle compound.

According to an aspect of the present disclosure, there is provided a method for labeling a radioisotope including: providing a diaminophenyl compound represented by Chemical Formula I below and including a biomolecule, a fluorescent dye or a nanoparticle compound bound thereto; and reacting the diaminophenyl compound and a radioisotope-labeled aldehyde compound represented by Chemical Formula II below at room temperature, Chemical Formula I

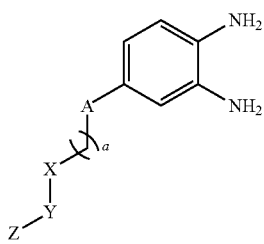

in Chemical Formula I,

A is CH$_2$ or O; a is 0 or an integer of 1 to 10; X is CH$_2$ or —CONH—; Y is CH$_2$ or

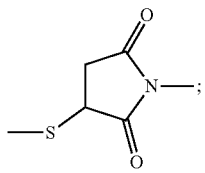

and Z is the biomolecule, the fluorescent dye or the nanoparticle compound,

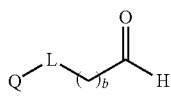

in Chemical Formula II, b is 0 or an integer of 1 to 10; and L is CH$_2$ or —CONH—;

Q is

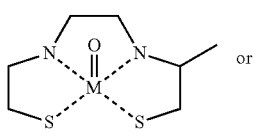,

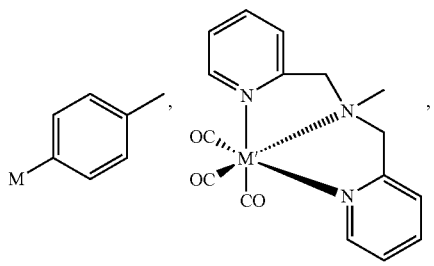,

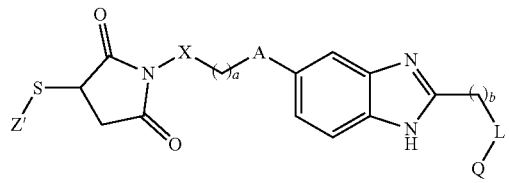 or

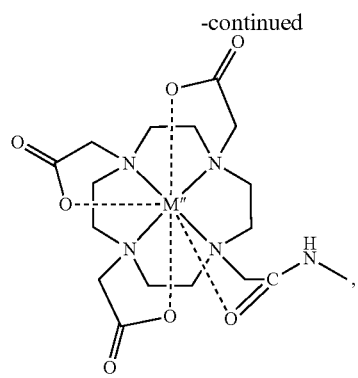

M, M' and M" in Q are radioisotopes.

According to an aspect of the present disclosure, there is provided a radiolabeling compound for labeling a molecule having an amine moiety, the radiolabeling compound represented by Chemical Formula II and including a radioisotope-labeled aldehyde compound.

According to an aspect of the present disclosure, there is provided a kit for labeling a radioisotope including: a diaminophenyl compound represented by Chemical Formula I and including a biomolecule, a fluorescent dye or a nanoparticle compound bound thereto; and a radioisotope-labeled aldehyde compound represented by Chemical Formula II.

According to an aspect of the present disclosure, there is provided a radiolabeling compound for labeling a molecule having a thiol moiety, the radiolabeling compound represented by Chemical Formula III below and provided for labeling a molecule having a thiol moiety:

Chemical Formula III

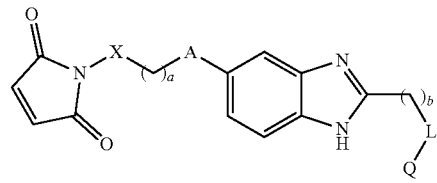

in Chemical Formula III, A, a, X, b, L, Q, and, M, M', and M" in Q are the same as defined above.

According to an aspect of the present disclosure, there are provided a radioisotope-labeled biomolecule, a radioisotope-labeled fluorescent dye or a radioisotope-labeled nanoparticle compound, represented by Chemical Formula IV below:

Chemical Formula IV

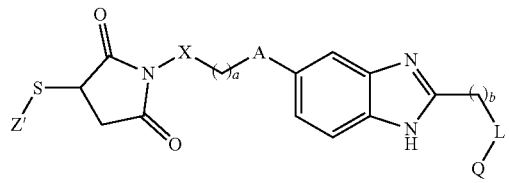

in Chemical Formula IV, A, a, X, b, L, Q, and, M, M', and M" in Q are the same as defined above, and Z' is a structure excluding a thiol group in a biomolecule, fluorescent dye or nanoparticle compound including the thiol group or substituted with the thiol group.

According to an aspect of the present disclosure, there is provided a composition for medical diagnosis including: a radioisotope-labeled biomolecule, a radioisotope-labeled fluorescent dye or a radioisotope-labeled nanoparticle compound represented by Chemical Formula IV as described above, as an active ingredient.

BRIEF DESCRIPTION OF DRAWINGS

The above and other aspects, features and other advantages of the present invention will be more clearly understood from the following detailed description taken in conjunction with the accompanying drawings, in which:

FIGS. 1A-1C show radio or UV/VIS-HPLC chromatogram, wherein FIG. 1A shows a radio-HPLC chromatogram for a crude product [$^{125}$I]5, FIG. 1B shows a radio-HPLC chromatogram for a purified product [$^{125}$I]5, and FIG. 1C shows a UV/VIS-HPLC chromatogram for compound 5;

DETAILED DESCRIPTION

Figure 2:
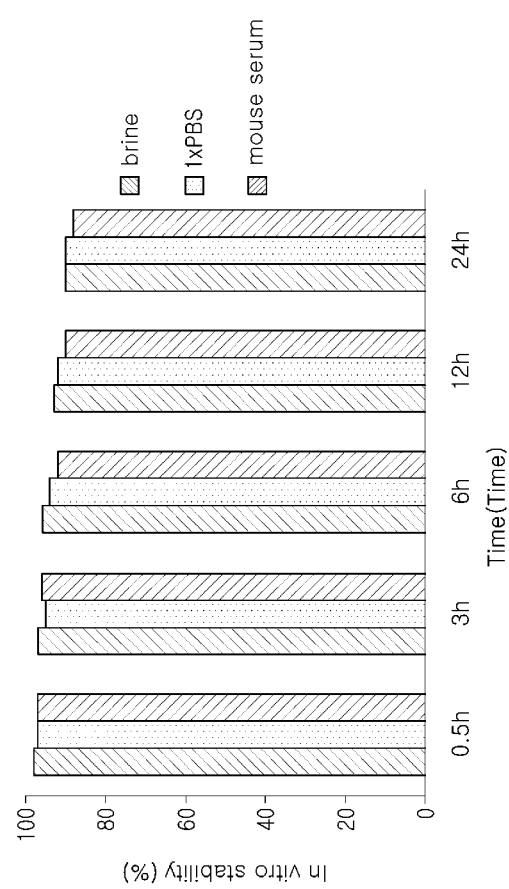
FIG. 2 shows in vitro stability of the [$^{125}$I]5 compound in a variety of media at 37° C.

Hereinafter, preferable embodiments of the present disclosure will be described in detail with reference to the accompanying drawings. However, the embodiments of the present disclosure may be modified in many different forms and the scope of the disclosure should not be limited to the embodiments set forth herein.

According to the present disclosure, there is provided a radioisotope-labeled aldehyde compound with markedly improved accumulation on the thyroid, and the compound may also be referred to as a "tracer". The tracer of the present disclosure may label a radioisotope with a rapid reaction rate and a high radiochemical yield through a condensation reaction with a biomolecule, a fluorescent dye or a nanoparticle including a diaminophenyl moiety.

More specifically, the method for labeling a radioisotope of the present disclosure is to use a condensation reaction of aldehyde-diamine, and includes providing a diaminophenyl compound represented by Chemical Formula I below and including a biomolecule, a fluorescent dye or a nanoparticle compound bound thereto; and reacting the diaminophenyl compound and a radioisotope-labeled aldehyde compound represented by Chemical Formula II below at room temperature, Chemical Formula I

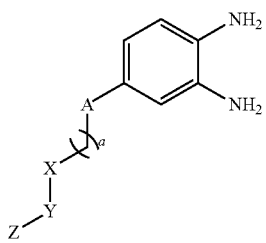

A is $CH_2$ or O; a is 0 or an integer of 1 to 10; X is $CH_2$ or —CONH—; Y is $CH_2$ or

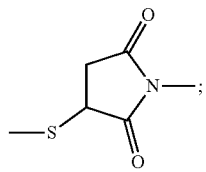

and Z is the biomolecule, the fluorescent dye or the nanoparticle compound,

Chemical Formula II

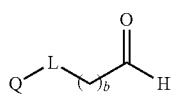

in Chemical Formula II, b is 0 or an integer of 1 to 10; and L is $CH_2$ or —CONH—; and
Q is

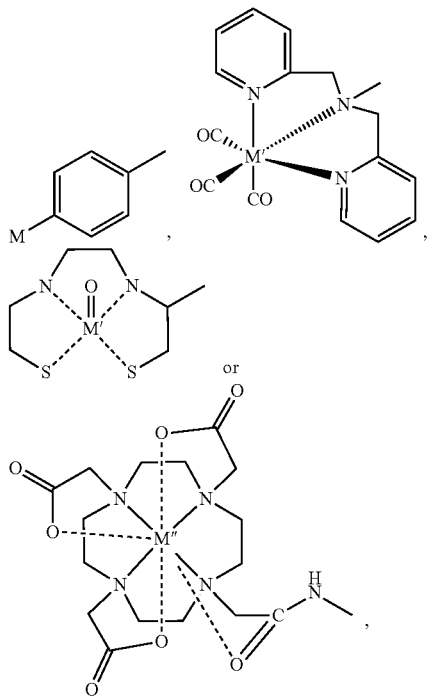

M, M' and M" in Q are radioisotopes.

That is, the present disclosure may be obtained by reacting the biomolecule, fluorescent dye or nanoparticle compound as described above and an aldehyde compound at room temperature, and there are advantages in that it is not required to use a high temperature reaction, an acidic or basic condition, a toxic reaction solvent, or the like. Here, the room temperature may be 10 to 40° C., for example, 25 to 35° C.

The pH condition for obtaining the compound is not particularly limited to pH of 1 to 14, but is preferably pH close to neutrality, for example, pH of 6 to 8.

The solvent that may be used in the reaction of the present disclosure is not particularly limited, but is preferably a water-soluble solvent, and may be, for example, dimethylsulfoxide (DMSO), dimethylformamide (DMF), tetrahydrofuran (THF), or the like.

Further, an aldehyde-diamine condensation reaction product obtained by the method for labeling a radioisotope according to the present disclosure exhibited stable characteristics in vivo, and was radioisotope-labeled with the bound diaminophenyl compound.

A catalyst may be used when reacting the diaminophenyl compound and the radioisotope-labeled aldehyde compound at room temperature. For example, the catalyst may be copper sulfate ($CuSO_4$), or the like, as a $Cu^{+2}$-based catalyst, but is not limited thereto.

The process of the method for labeling a radioisotope of the present disclosure may be schematically shown as the following Scheme (I), and this reaction may be obtained at a yield of about 67 to 99%.

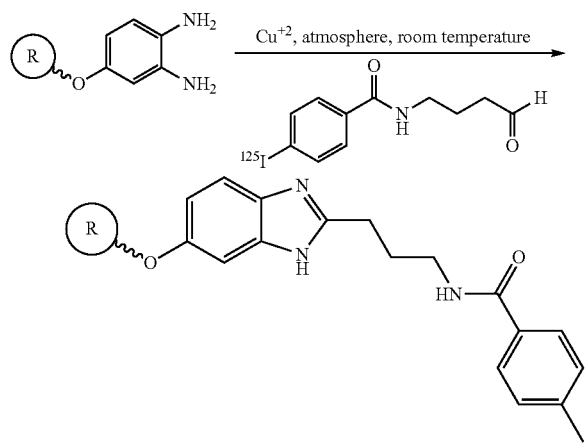

Meanwhile, the providing of the diaminophenyl compound may include providing a compound represented by Chemical Formula Ia below and including a thiol moiety; and reacting the compound represented by Chemical Formula Ia below and a compound represented by Chemical Formula Ib below to obtain the compound represented by Chemical Formula I above, Z'—SH  [Chemical Formula Ia]

in Chemical Formula Ia, Z' is the same as a structure except for a —SH moiety in Z when the biomolecule, fluorescent dye, or nanoparticle compound represented by Z in Chemical Formula I includes a thiol moiety; and Z' is the same as Z when the biomolecule, fluorescent dye or nanoparticle compound represented by Z does not include a thiol moiety.

That is, in the present disclosure, the biomolecule, the fluorescent dye or the nanoparticle compound including the thiol group or substituted with the thiol group has a structure represented by Chemical Formula Ia below:

Chemical Formula Ib

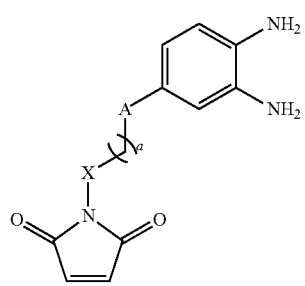

in Chemical Formula Ib, A, a and X are the same as defined in Chemical Formula I.

Here, the reaction between the compound represented by Chemical Formula Ia and the compound represented by Chemical Formula Ib is preferably performed under a $Cu^{+2}$-based catalyst at room temperature and in atmospheric pressure.

That is, the compound represented by Chemical Formula I of the present disclosure may be designed so that the diaminophenyl compound including various desired biomolecules, fluorescent dyes or nanoparticle compounds may be easily obtained by reacting the biomolecule, the fluorescent dye or the nanoparticle compound including a thiol moiety with the structure of Chemical Formula Ib.

Thus, the providing of the compound represented by Chemical Formula Ia above and including a thiol moiety may be directly applied to, for example, a peptide, a proteome, or the like, having cysteine C when the biomolecule, the fluorescent dye or the nanoparticle compound includes a thiol moiety, and further include providing the compound represented by Chemical Formula Ia by substituting a thiol moiety into Z' when the biomolecule, the fluorescent dye or the nanoparticle compound does not include a thiol moiety.

The biomolecule may be at least one selected from the group consisting of a peptide, an affibody, an antibody, and an oligonucleotide; the nanoparticle may be at least one selected from the group consisting of a metal nanoparticle, a synthetic polymer nanoparticle, and a biopolymer nanoparticle; the metal nanoparticle may be any one metal selected from the group consisting of gold (Au), platinum (Pt), palladium (Pd), silver (Ag), and copper (Cu); or any one metal oxide selected from the group consisting of cobalt (Co), manganese (Mn), iron (Fe), nickel (Ni), gadolinium (Gd), molybdenum (Mo), zinc (Zn), and chromium (Cr). Meanwhile, the fluorescent dye may be at least one selected from the group consisting of a cyanine-based dye, a fluorescein-based dye, and a rhodamine-based dye.

Here, examples of the peptide may include RGD peptide, CGNSNPKSC peptide (SEQ ID NO: 1), VHSPNKK peptide (SEQ ID NO: 2), CTTHWGFTLC peptide (SEQ ID NO: 3), SGKGPRQITAL peptide (SEQ ID NO: 4), SGRSA peptide (SEQ ID NO: 5), FSRYLWS peptide (SEQ ID NO: 6), and the like, preferably RGD peptide, as a tumor targeting peptide.

In addition, the affibody is not limited, but may be a small molecule within 7 KDa that may be bound to proteins such as Aβ peptides, Apolipo protein A1, CD25, CD28, c-Jun, EGFR, Factor VIII, Fibrinogen, Gp120, HER2, IgA, IgE, IgM, IL-8, insulin, RSV G protein, Taq polymerase, TNF-α, transferrin, transthyretin, and the like.

Further, the antibody is not limited, but may be anti-VEGFR, anti-ERBB2, anti-CD20, anti-CD19, anti-CD22, anti-CD33, anti-CD25, anti-HLA-DR 10β, anti-tenascin, anti-CEA, anti-MUC1, anti-TAG 72, or the like.

Further, the oligonucleotide is not limited, but may be DNA, RNA, siRNA, antisense oligonucleotide, or the like.

The metal nanoparticle is not limited, but may be a metal such as gold (Au), platinum (Pt), palladium (Pd), silver (Ag), copper (Cu), or the like; or a metal oxide such as cobalt (Co), manganese (Mn), iron (Fe), nickel (Ni), gadolinium (Gd), molybdenum (Mo), zinc (Zn), chromium (Cr), or the like, but preferably a gold nanoparticle or an iron nanoparticle.

Further, the synthetic polymer nanoparticle is not limited, but may be poly(ethylene glycol), poly(vinyl alcohol), poly (acrylic acid), poly(hydroxyester), poly(ε-caprolactone), poly(orthoester), polanhydride, polyphosphagene, poly(propylenefumarate), poly(glycolic acid), poly(lactic acid), poly(lactic-co-glycolic acid), poly(hydroxybutyate), poly(hydroxybutyrate-co-valerate), poly(urethane), poly(methyl methacrylate), or the like.

Further, the biopolymer nanoparticle is not limited, but may be chitin, chitosan, polylysine, hyaluronic acid, alginic acid, dextran, cellulose, or the like.

Further, the nanoparticle is a nanoparticle having a size of 1 nm to 1000 nm, preferably 10 nm to 500 nm, and more preferably 50 nm to 200 nm. When the size of the nanoparticle is less than 1 nm, it is difficult to produce the radioactive iodine-labeled nanoparticle according to the present disclosure. When the size of the nanoparticle is more than 1000 nm, inherent characteristics of the nanoparticle may be lost.

Meanwhile, the fluorescent dye may be at least one selected from the group consisting of a cyanine-based dye, a fluorescein-based dye, and a rhodamine-based dye.

The radioisotope that may be applied to the present disclosure may be selected from the group consisting of I, F, Tc, Re, Ga, In, Zr, Y, Ho, Sm and Lu. For example, the radioisotope may include all of I-125, F-18, Sc-44, Ga-67, Ga-68, Zr-89, Tc-99m, In-111, and the like, which are diagnostic radioisotopes, and Sc-47, Y-90, Sm-153, Ho-166, Lu-177, Re-188, Pb-212, Bi-213, Th-232, and the like, which are therapeutic radioisotopes. Meanwhile, the radioisotope that may be applied to the present disclosure is not limited thereto, and includes, without limitation, an alpha-emitting radionuclide and a beta-emitting radionuclide, which are the therapeutic radioisotopes used for treatment of cancer, or the like, and a positron emitting radionuclide and a gamma-emitting radionuclide, which are the diagnostic radioisotopes used for diagnosis.

Here, the radioisotope M is I or F, M' is an element selected from the group consisting of Tc and Re, and M" may be an element selected from the group consisting of Ga, In, Y and Zr.

The radioactive iodine may be at least one radioactive iodine selected from the group consisting of, for example, $^{122}$I, $^{123}$I, $^{124}$I, $^{125}$I, $^{127}$I, $^{131}$I, and $^{132}$I, and preferably $^{125}$I.

According to another aspect of the present disclosure, there is provided a radiolabeling compound for labeling a molecule having an amine moiety, the radiolabeling compound including an aldehyde moiety and represented by Chemical Formula II below:

Chemical Formula II

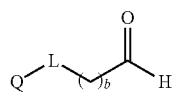

in Chemical Formula II, b is 0 or an integer of 1 to 10; and L is CH$_2$ or —CONH—;

Q is

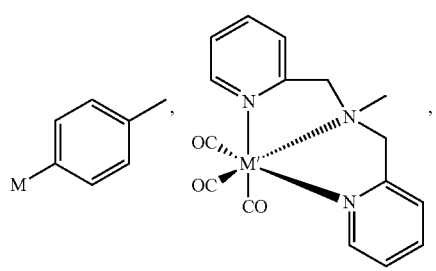

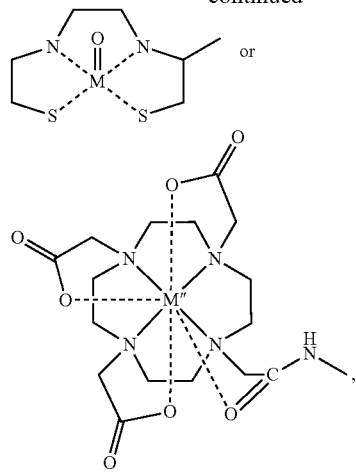

M, M' and M" in Q are radioisotopes.

The compound represented by Chemical Formula II may preferably have the same structure as Chemical Formula IIa, wherein M may be radioactive iodine.

Chemical Formula IIa

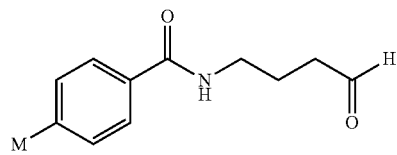

As described above, the radioisotope-labeled aldehyde compound used in the present disclosure may be applied as a radiolabeling compound for labeling a molecule having an amine moiety, such as a diamine moiety, and preferably a diaminophenyl moiety.

According to another aspect of the present disclosure, there is provided a kit for labeling a radioisotope including: a diaminophenyl compound represented by Chemical Formula I below and including a biomolecule, a fluorescent dye or a nanoparticle compound bound thereto; and a radioisotope-labeled aldehyde compound represented by Chemical Formula II below. The kit for labeling a radioisotope of the present disclosure is based on a method for labeling a radioisotope of the present disclosure described above, and contents described in the method for labeling a radioisotope may be equally applied to the kit for labeling a radioisotope.

Chemical Formula I

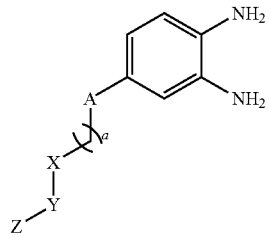

In Chemical Formula 1, A is CH$_2$ or O; a is 0 or an integer of 1 to 10; X is CH$_2$ or —CONH—; Y is CH$_2$ or

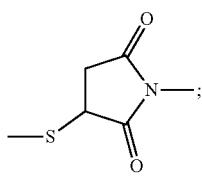

and Z is the biomolecule, the fluorescent dye or the nanoparticle compound,

[Chemical Formula II]

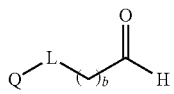

in Chemical Formula II, b is 0 or an integer of 1 to 10; and L is CH$_2$ or —CONH—; and Q is

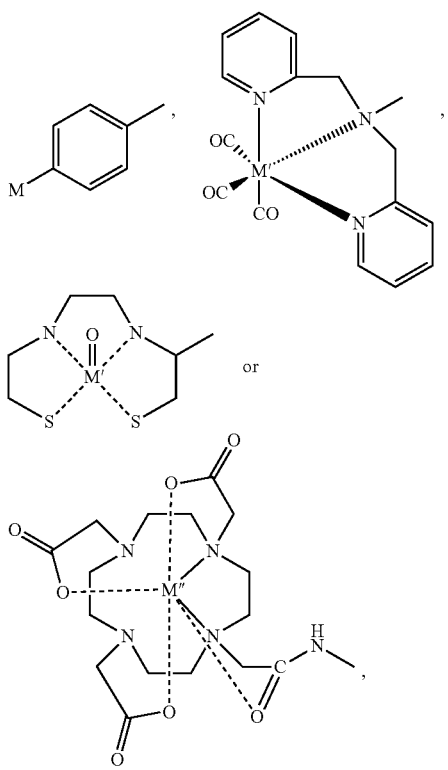

M, M' and M" in Q are radioisotopes.

In other words, the biomolecule may be at least one selected from the group consisting of a peptide, an affibody, an antibody, and an oligonucleotide; the nanoparticle may be at least one selected from the group consisting of a metal nanoparticle, a synthetic polymer nanoparticle, and a biopolymer nanoparticle; the metal nanoparticle may be any one metal selected from the group consisting of gold (Au), platinum (Pt), palladium (Pd), silver (Ag), and copper (Cu); or any one metal oxide selected from the group consisting of cobalt (Co), manganese (Mn), iron (Fe), nickel (Ni), gadolinium (Gd), molybdenum (Mo), zinc (Zn), and chromium (Cr), and the fluorescent dye may be at least one selected from the group consisting of a cyanine-based dye, a fluorescein-based dye, and a rhodamine-based dye.

The radioisotope is also not particularly limited, and may be, as described in the method for labeling a radioisotope of the present disclosure, selected from the group consisting of I, F, Tc, Re, Ga, In, Zr, Y, Ho, Sm and Lu. For example, the radioisotope may include all of I-125, F-18, Sc-44, Ga-67, Ga-68, Zr-89, Tc-99m, In-111, and the like, which are diagnostic radioisotopes, and Sc-47, Y-90, Sm-153, Ho-166, Lu-177, Re-188, Pb-212, Bi-213, Th-232, and the like, which are therapeutic radioisotopes. Meanwhile, the radioisotope that may be applied to the present disclosure is not limited thereto, and includes, without limitation, an alpha-emitting radionuclide and a beta-emitting radionuclide, which are the therapeutic radioisotopes used for treatment of cancer, or the like, and a positron emitting radionuclide and a gamma-emitting radionuclide, which are the diagnostic radioisotopes used for diagnosis.

Here, the radioisotope M is I or F, M' is an element selected from the group consisting of Tc and Re, and M" may be an element selected from the group consisting of Ga, In, Y and Zr.

The radioactive iodine may be at least one radioactive iodine selected from the group consisting of, for example, $^{122}$I, $^{123}$I, $^{124}$I, $^{125}$I, $^{127}$I, $^{131}$I, and $^{132}$I, and preferably $^{125}$I.

According to another aspect of the present disclosure, there is provided a radiolabeling compound for labeling a molecule having a thiol moiety, the radiolabeling compound represented by Chemical Formula III below:

Chemical Formula III

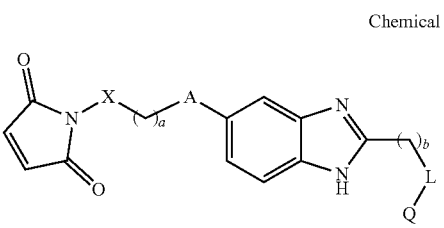

in Chemical Formula III, A is CH$_2$ or O; a is 0 or an integer of 1 to 10; X is CH$_2$ or —CONH—; b is 0 or an integer of 1 to 10; and L is CH$_2$ or —CONH—; and Q is

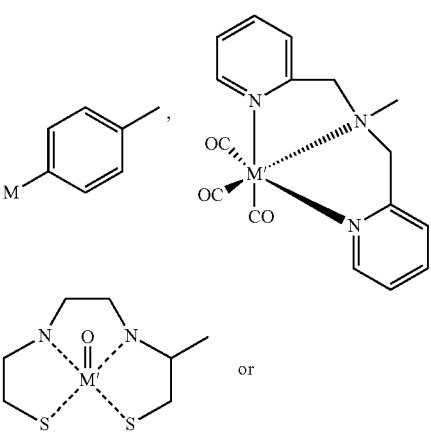

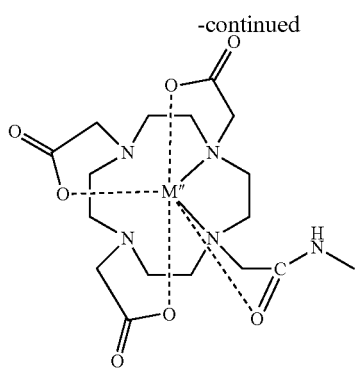

M, M' and M" in Q are radioisotopes.

The radiolabeling compound represented by Chemical Formula III may be used as a radiolabeling compound for labeling a molecule having a thiol moiety. The radiolabeling compound represented by Chemical Formula (III) includes a maleimide moiety to be specifically bound to the thiol moiety, and thus, for example, the radiolabeling compound may be selectively bound to a peptide and a proteome in which one of components of the amino acid sequence has cysteine (C). Otherwise, in the case of a biomolecule, a fluorescent dye or a nanoparticle compound without the thiol moiety, the radiolabeling compound of the present disclosure may be used by substituting the thiol moiety into the biomolecule, the fluorescent dye or the nanoparticle compound.

According to another aspect of the present disclosure, there is provided a radioisotope-labeled biomolecule, a radioisotope-labeled fluorescent dye or a radioisotope-labeled nanoparticle compound, represented by Chemical Formula IV below:

Chemical Formula IV

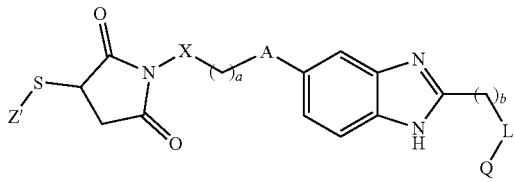

in Chemical Formula IV, A is $CH_2$ or O; a is 0 or an integer of 1 to 10; X is $CH_2$ or —CONH—; Z' is a structure excluding a thiol group in a biomolecule, fluorescent dye or nanoparticle compound including the thiol group or substituted with the thiol group; b is 0 or an integer of 1 to 10; and L is $CH_2$ or —CONH—;

Q is

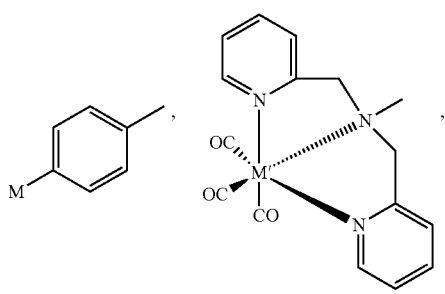

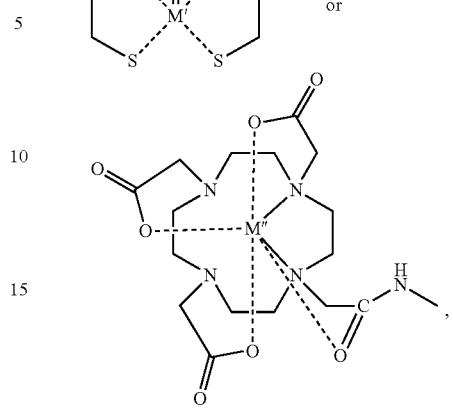

M, M' and M" in Q are radioisotopes.

According to another aspect of the present disclosure, there is provided a composition for medical diagnosis and treatment including: the radioisotope-labeled biomolecule, a radioisotope-labeled fluorescent dye or a radioisotope-labeled nanoparticle compound represented by Chemical Formula IV as described above, as an active ingredient.

The medical diagnosis is not particularly limited, but may be a diagnosis by single photon emission computed tomography (SPECT), positron emission tomography (PET), micro-PET, computed tomography (CT), magnetic resonance imaging (MRI) or target imaging of radiological diagnostic equipment.

The method for labeling a radioactive iodine according to the present disclosure may be used to label a biomolecule, a fluorescent dye, a nanoparticle compound or a combination thereof with radioactive iodine, using the compound represented by Chemical Formula I and/or II. The method may perform a reaction proceeding at a rapid rate within 30 to 60 minutes and simultaneously exhibit a high radiochemical yield value of 67% or more. Therefore, the method may be usefully used as a radioactive iodine labeling method.

Thus, according to the present disclosure, it is expected that a radioactive iodine-labeled product may be effectively obtained for various target compounds, for example, peptides and the like. Further, this result is expected to lead to development of radioactive pharmaceuticals that may be utilized in clinical use as well as future study.

Hereinafter, the present disclosure is described in more detail with reference to Inventive Examples. The following Inventive Examples are provided for illustrative purposes only, and the scope of the present disclosure is not limited thereto.

INVENTIVE EXAMPLES

1. Synthesis of $^{125}$I-Labeled Compound
(1) Synthesis of $^{125}$I-Labeled Aldehyde For synthesis of $^{125}$I-labeled aldehyde [$^{125}$I] 5, specific radioactive analogue 4-iodo-N-(4-oxobutyl) benzamide) 5 was synthesized by coupling of 4-aminobutyraldehyde diethyl acetal with 4-iodobenzoic acid under basic conditions and a subsequent reduction under acidic conditions (Scheme 1). The radioiodination shown in 6 was achieved using [$^{125}$I] NaI and chloramines-T as oxidants (Scheme 3). The radioiodination reaction was terminated by adding an aqueous solution of sodium metabisulfite. After HPLC purification of the crude product, [$^{125}$I] 5 was obtained with high radiochemical yield (72±6%, n=5). The specific activity was 45 GBq/μmol and the chemical purity was more than 99%. In the HPLC chromatogram of the crude mixture, the main product [$^{125}$I] 5 was clearly shown at 22.6 minutes (FIG. 1). Radio-labeling reactions were performed by using various amounts of radioisotopes (100 μCi to 1 mCi), but the radiochemical results were consistent. The radioactive iodine compound [$^{125}$I] 5 was found to be stable for more than 6 months in the refrigerator (4° C.), and the radioactive iodine compound [$^{125}$I] 5 was not hydrolyzed unlike conventionally used active ester-based prosthetic groups (Bolton-Hunter-reagent). The compound [$^{125}$I] 5 was shown to be stable in various media including PBS, saline, and mouse serum, at 37° C. for 24 hours or more, which was confirmed using radio-HPLC (FIG. 2).

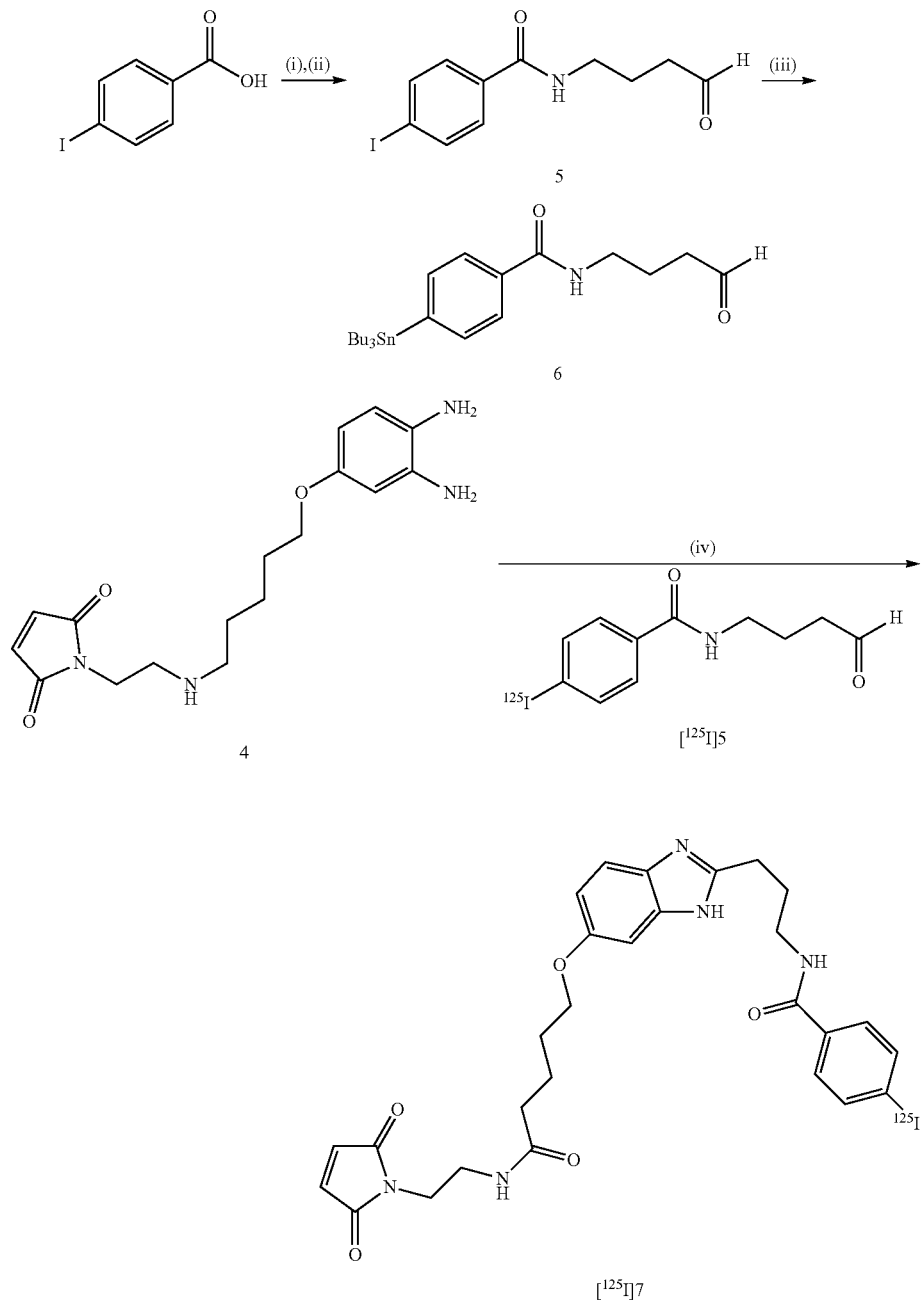

Scheme 1: Synthesis of Compound 5 and Compound 7

Reagents and conditions: (i) HBTU, DIPEA, 4-aminobutyraldehyde diethyl acetal, at room temperature, for 2 hours, (ii) acid hydrolysis, (iii) Pd(Ph$_3$P)$_4$, bis (tributyltin), 1,4-dioxane, and reflux, and (iv) Cu$^{+2}$, pH 7.5, at room temperature, for 2 hours, air.

(2) Synthesis of Maleimide-Based Aryldiamine Linker
The aryl diamine compound 4 disclosed in the above (1) was synthesized by the following Scheme 2.

Scheme 2: Synthesis of Compound 4

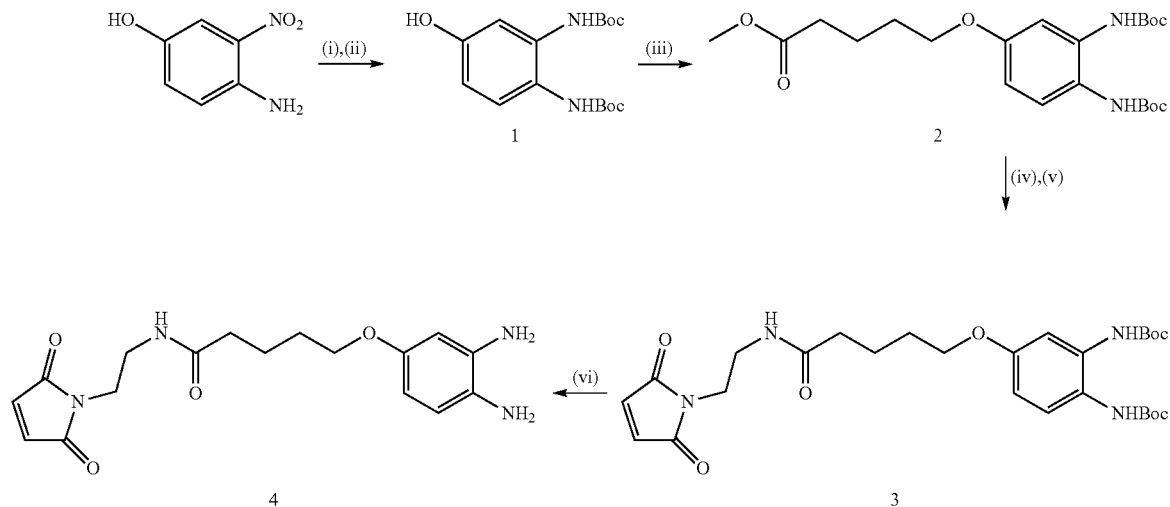

Reagents and conditions: (i) Zn/HCOOH, MeOH, for 1 hour, (ii) (Boc)$_2$O, H$_2$O, at room temperature, for 2 hours,
(iii) methyl 5-bromo valerate, K$_2$CO$_3$, DMF, at room temperature, for 24 hours, and (iv) LiOH, dioxane/H$_2$O, at room temperature,
for 2 hours, (V) HBTU, DIPEA, at room temperature, N-(2-aminoethyl)-maleimide trifluoromethylacetate, and (vi) HCl, Et$_2$O, for 2 hours.

(3) Radiosynthesis of Radioisotope-Labeled Compound 7

The aldehyde diamine coupling reaction was performed using the radioiodinated compound [$^{125}$I] 5 and the diamine group-containing compound 4. An aryldiamine ring supplemented with an electron withdrawing group (—OCH$_2$—) was selected to accelerate the coupling reaction. A non radioactive analogue 7 was synthesized for HPLC identification and investigation of characteristics of [$^{125}$I] 7 prior to the radiosynthesis of the desired compound [$^{125}$I] 7. Compound 7 was synthesized by stirring compounds 4 and 5 in the presence of a catalytic amount of copper sulfate at room temperature and in the atmosphere (in the presence of oxygen). The radiolabeling reaction was performed by mixing various concentrations of 5-(3,4-diaminophenoxy)-N-(2-(2,5-dioxo-2,5-dihydro-1H-pyrrol-1-yl)ethyl)pentanamide 4 (5, 25 and 50 μM) and 100 μCi of [$^{125}$I] 5 at room temperature. The reactions were monitored at different time points using radio-HPLC, and showed radiochemical yields summarized in Table 1. 99% and 91% or more of the desired compounds [$^{125}$I] 7 were obtained within 30 minutes at room temperature using 50 μM and 25 μM of the aryl diamine compounds 4, respectively (Entries 2 and 3). In addition, 80% or more of [$^{125}$I] 5 was converted to [$^{125}$I] 7 within 30 minutes using 5 μM of substrate 4 (Entry 4). When 50 μM of precursor 4 was used, the reaction at 5 minutes was slow (Entry 1), but high radiochemical yield was observed after 30 minutes post incubation (Entry 3). The radiochemical yield and reaction kinetics were found to be comparable to a number of bioconjugate reactions given in the document.

Scheme 3: Radiosynthesis of linker [$^{125}$I] 5 compound and radiolabeling compound 7

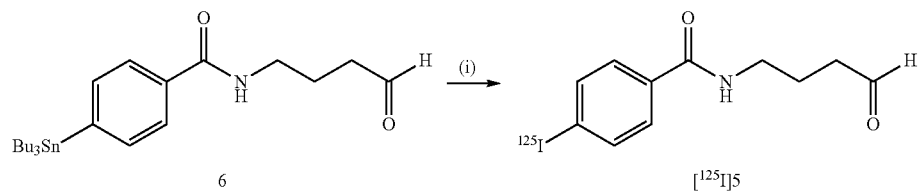

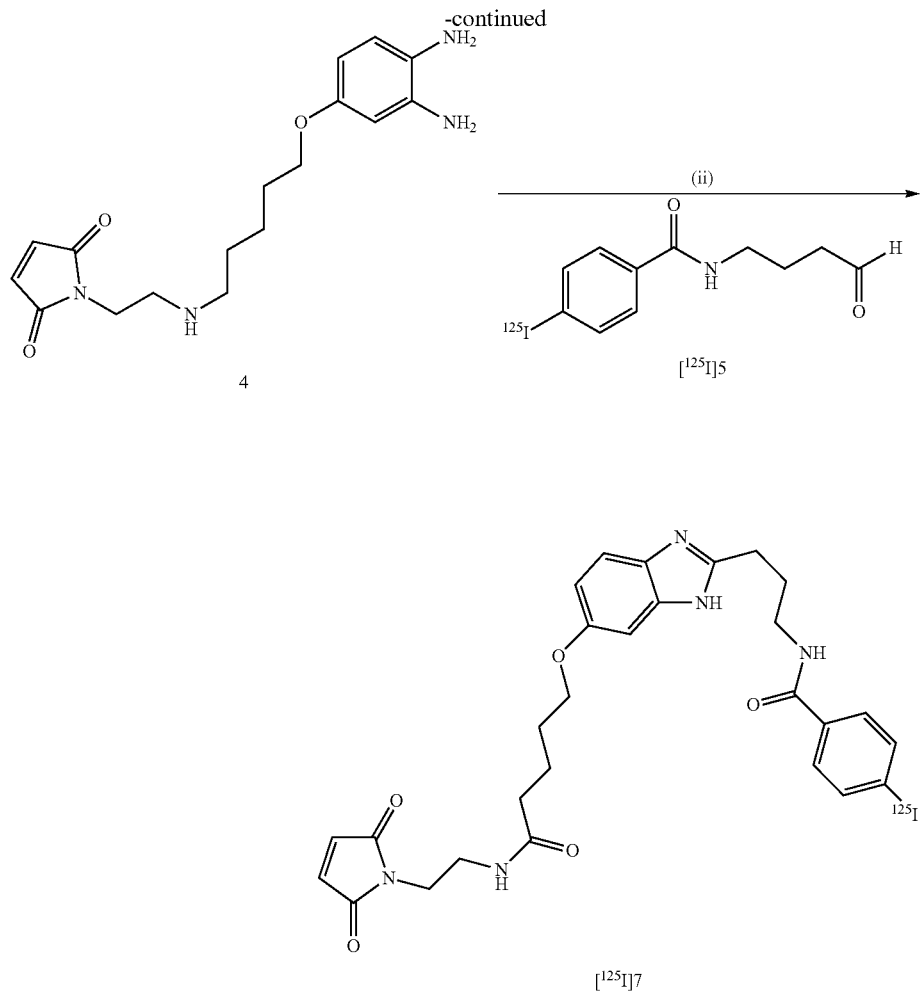

Reagents and conditions: (i) [$^{125}$I] NaI, chloramine-T, DMSO, at room temperature, for 10 minutes, and (ii) Cu$^{+2}$, pH 7.5, at room temperature, air

2. Preparation of $^{125}$I-Labeled cRGD Peptide ([$^{125}$I] 8)

The following Scheme 4 shows a process for labeling a cyclic RGD peptide, which is widely used in biological study and clinical use as a cancer targeting peptide, with radioactive iodine, utilizing the radiolabeling compound [$^{125}$I] 5 of the present disclosure synthesized in the above 1.

TABLE 1

Radiolabeling results of [$^{125}$I] 7 and [$^{125}$I] 8

| Entry[a] | Concentration[b] (μmol) | Substrate | Time (min) | Product | % RCY[c] |
|---|---|---|---|---|---|
| 1 | 50 | 4 | 5 | [$^{125}$I]7 | 26 |
| 2 | 50 | 4 | 30 | [$^{125}$I]7 | >99 |
| 3 | 25 | 4 | 30 | [$^{125}$I]7 | 91 |
| 4 | 5 | 4 | 30 | [$^{125}$I]7 | 80 |
| 5 | 50 | 8 | 30 | [$^{125}$I]8 | >99 |
| 6 | 25 | 8 | 30 | [$^{125}$I]8 | 93 |
| 7 | 5 | 8 | 30 | [$^{125}$I]8 | 69 |

[a]Solvent: DMSO/PBS, Cu$^{+2}$ (0.1 eq), 25° C.,
[b]final concentration in reaction mixture, and
[c]Radiochemical yield determined by radio-HPLC The radiolabeled cRGD peptide has high binding affinity and selectivity for the $\alpha_v\beta_3$ receptors and is extensively used to detect metastatic diseases and rapidly growing cancers in preclinical studies. Many radiolabeled cRGD peptides have been developed for SPECT or PET-based studies of tumor models. The present inventors also selected cRGD as a model peptide in order to test efficiency of the radioisotope labeling strategy. Radiosynthesis of the target compound [$^{125}$I] 8 is shown in the following Scheme 4. The radiolabeling reaction was performed by mixing different concentrations of aryl diamine installed cRGD 8 (5, 25 and 50 μM) with 100 μCi of [$^{125}$I] 5 at room temperature in the presence of a catalyst. The radioiodination reactions were monitored using radio-HPLC, and the observed radiochemical yields are summarized in Table 1 above. 99% or more of the compound [$^{125}$I] 8 was obtained within 30 minutes and at room temperature (Entry 5) using 50 μM of the target compound 8. Further, 93% and 69% of the compound [$^{125}$I] 8 were obtained from 25 μM and 5 μM of the compound 6, respectively. The radiolabeling reaction was neat and thus there was no side reaction in the radiolabeling reaction and only one radioiodinated product was observed in the radioactive HPLC chromatogram.

Scheme 4: Radiosynthesis of compound [$^{125}$I] 8$^a$

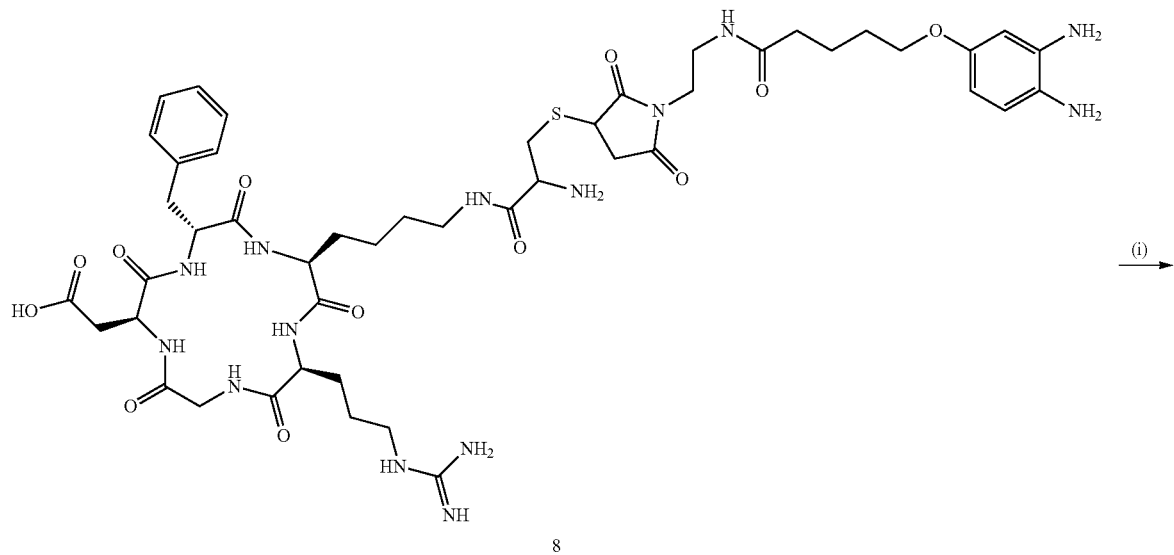

8

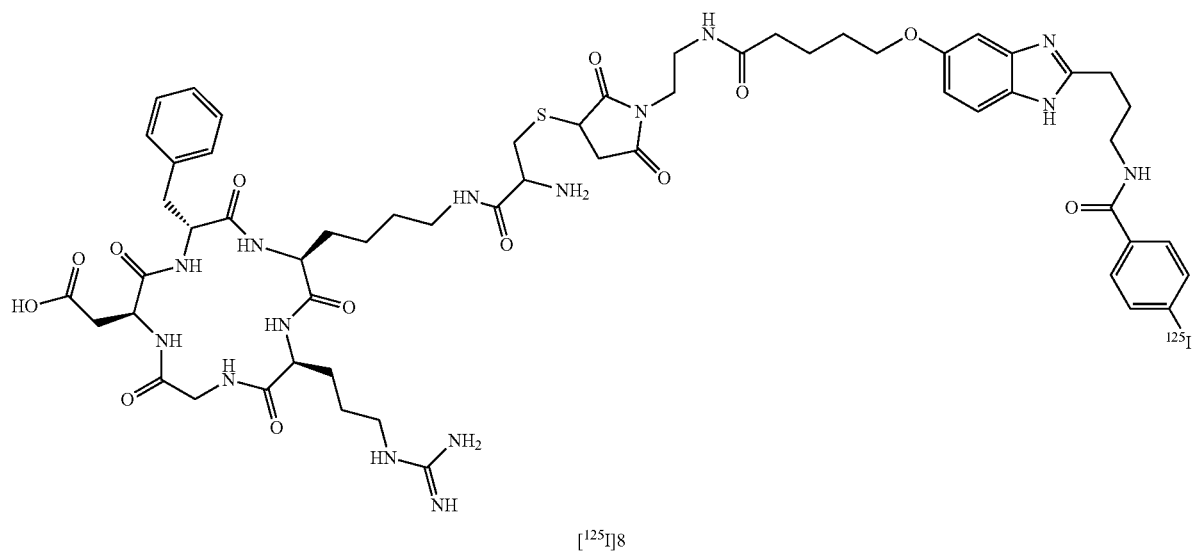

[$^{125}$I]8

$^a$ Reagents and conditions: (i) [$^{125}$I] 5, Cu$^{+2}$, at room temperature, air 3. Preparation of Radioisotope-Labeled HAS (1) Preparation of $^{125}$I-Labeled HSA ([$^{125}$I] 9)

In order to determine the radioisotope labeling efficiency of the aryldiamine alkylaldehyde coupling reaction, [$^{125}$I] 5 was treated with an aryldiamine containing human serum albumin protein 9. The human serum albumin protein is capable of not only being used as a drug delivery carrier, but also enhance the blood circulation time of rapidly clearing drugs. In the present experiment, maleimide-cysteine-34 conjugation was applied.

Scheme 5: Radioiodination of aryldiamine functionalized human serum albumin [$^{125}$I] 9$^a$

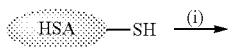

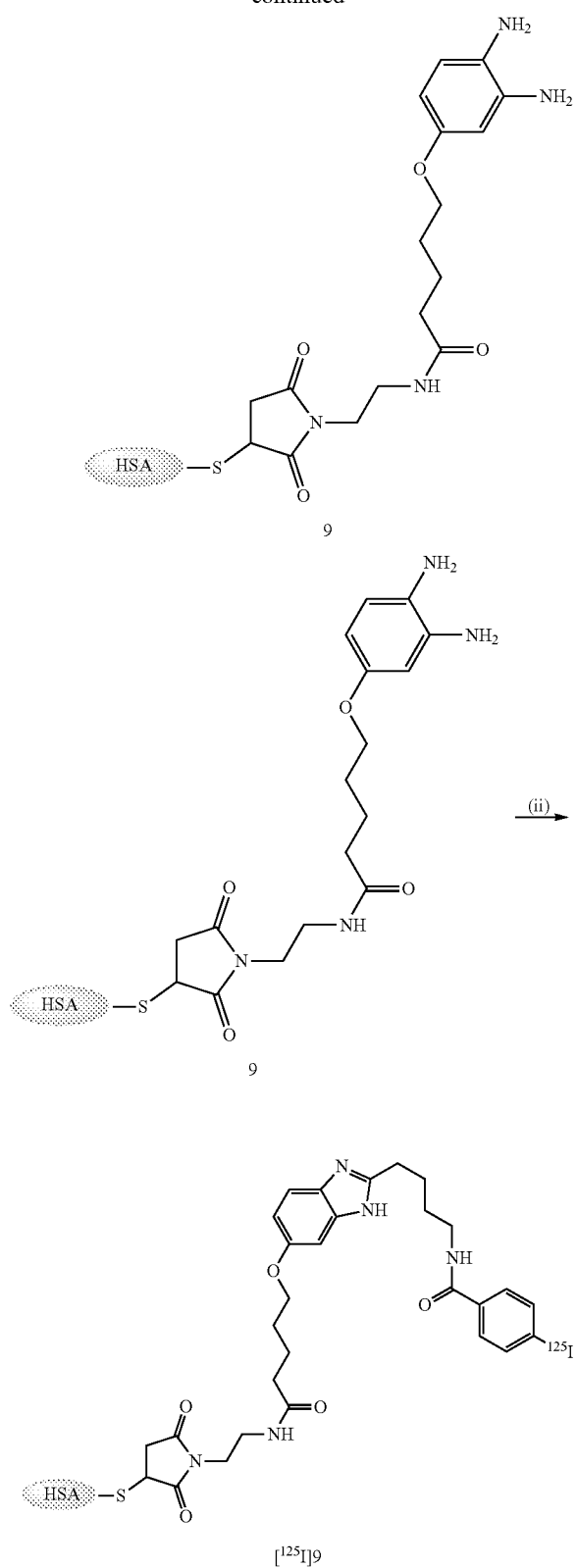

<sup>a</sup>Reagents and conditions: (i) PBS, at room temperature, pH 7.5, for 10 hours, and (ii) [<sup>125</sup>I] 5, Cu<sup>+2</sup>, air, at room temperature For chemical installation of the aryl diamine group to the HSA, 4 molar excess amount of maleimide containing the aryl diamine 4 was incubated with HSA in phosphate buffer saline of pH 7.5 for 10 hours at 25° C. At the end of the reaction, the mixture was passed through a PD-10 (size exclusion) column to obtain chemically substituted aryl diamine HSA. MALDI-Tof analysis confirmed purity and characteristics of the desired product. The results showed that 1.3 aryl diamine groups were conjugated with one HSA protein at room temperature. In order to determine the efficiency of the alkylaldehyde aryldiamine condensation reaction, various concentrations of aryldiamine installed HSA were incubation with 100 μCi of the $^{125}$I-labeled alkylaldehyde [$^{125}$I] 5 in the presence of a catalytic amount of CuSO$_4$ and oxygen. The radiochemical yield was determined using radio-TLC and summarized in Table 2 below. The conversion yield was dependent on concentration, and a radiochemical yield of 94% or more was obtained for 50 μM aryldiamine-modified HSA 9 within 2 hours (Entry 3). Under the same reaction conditions, 89% and 67% radiochemical yields were obtained for 25 μM and 5 μM of aryldiamine-modified HSA, respectively (Entries 4 and 5). In the control experiment, [$^{125}$I] 5 was incubated with unmodified pure HSA under the same conditions, but no nonspecific interaction was observed. Next, [$^{125}$] 9 was prepared for biodistribution studies through incubation of 1.0 mCi of $^{125}$I-labeled alkyl-aldehyde [$^{125}$I] 5 and 50 μM of aryldiamine-modified HSA 9 for 2 hours in the presence of the catalyst. The crude mixture was purified using a PD-10 desalting column to obtain [$^{125}$I] 9 with 90% isolated radiochemical yield and 99% or more radiochemical purity. In order to compare in vivo behavior, HSA was radioiodinated through tyrosine ring using [$^{125}$I] NaI and chloramine-T as oxidizing agent. $^{125}$I-HSA ([$^{125}$I] 10) was synthesized with 83% radiochemical yield and 99% radiochemical purity after purification through PD-10 column.

TABLE 2

In vitro radiolabeling results of aryldiamine-conjugated HSA when [$^{125}$I] 5 applied

| Entry[a] | Concentration of 9[b] (μmol) | Time (h) | % RCY[c] |
|---|---|---|---|
| 1 | 50 | 0.5 | 54 |
| 2 | 50 | 1 | 63 |
| 3 | 50 | 2 | 94 |
| 4 | 25 | 2 | 89 |
| 5 | 5 | 2 | 67 |

[a]Solvent: PBS, Cu$^{+2}$ (0.1 eq), 25° C.,
[b]final concentration in reaction mixture, and
[c]Radiochemical yield determined by radio-HPLC (2) Preparation of $^{99m}$Tc-Labeled HSA $^{99m}$Tc-labeled HSA was prepared as in Scheme 6 by a process similar to that described in the above (1).

The $^{99m}$Tc-labeled alkylaldehyde was reacted with HSA 9 for 2 hours at room temperature in the presence of a catalytic amount of CuSO$_4$, purified, and obtained with a radiochemical purity of 99% or more.

Scheme 6:
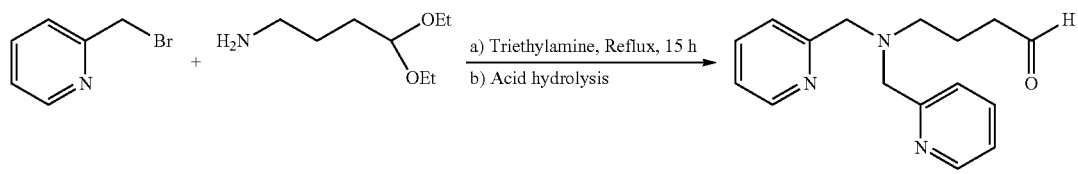
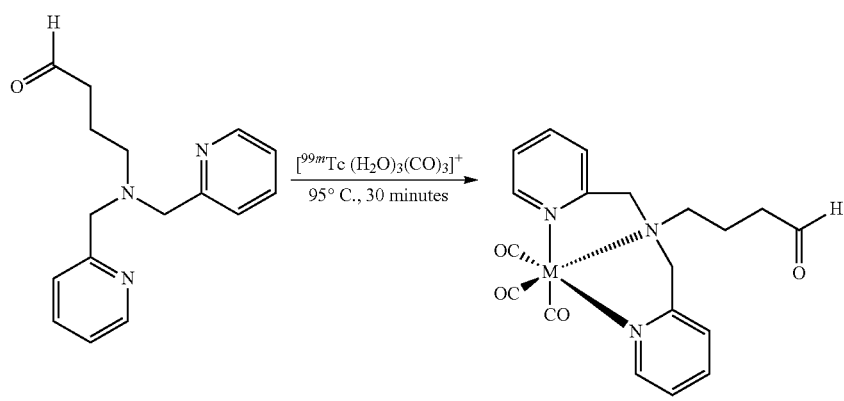
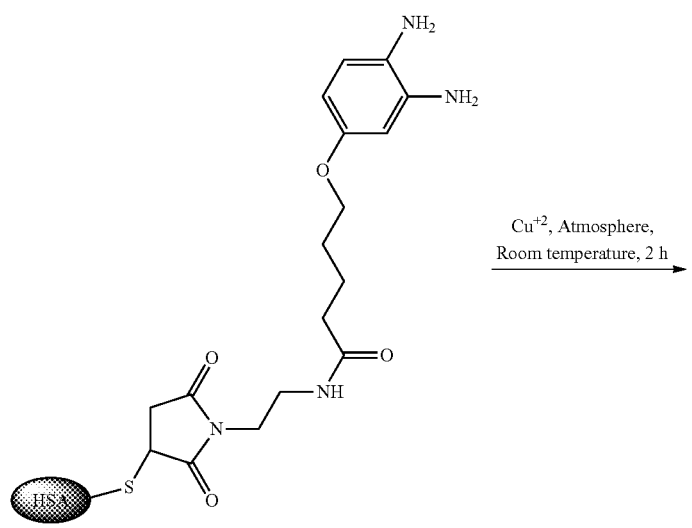

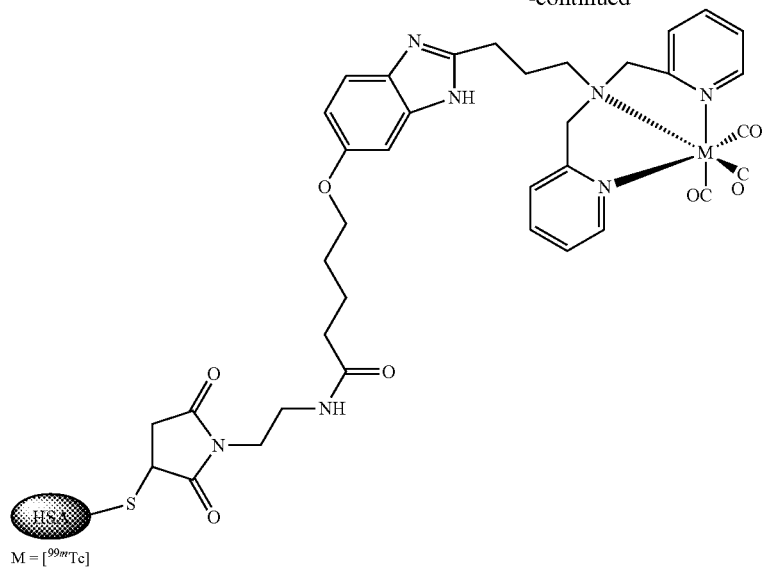

M = [⁹⁹ᵐTc]

(3) Preparation of ⁶⁸Ga, ¹¹¹In and ⁸⁹Zr-Labeled HSA

⁶⁸Ga, ¹¹¹In, and ⁸⁹Zr-labeled HSA were prepared as in Scheme 7 by a process similar to that described in the above (1).

The ⁶⁸Ga, ¹¹¹In, and ⁸⁹Zr-labeled HSA was reacted with HSA 9 for 2 hours at room temperature in the presence of a catalytic amount of $CuSO_4$, purified, and obtained with a radiochemical purity of 99% or more.

Scheme 7

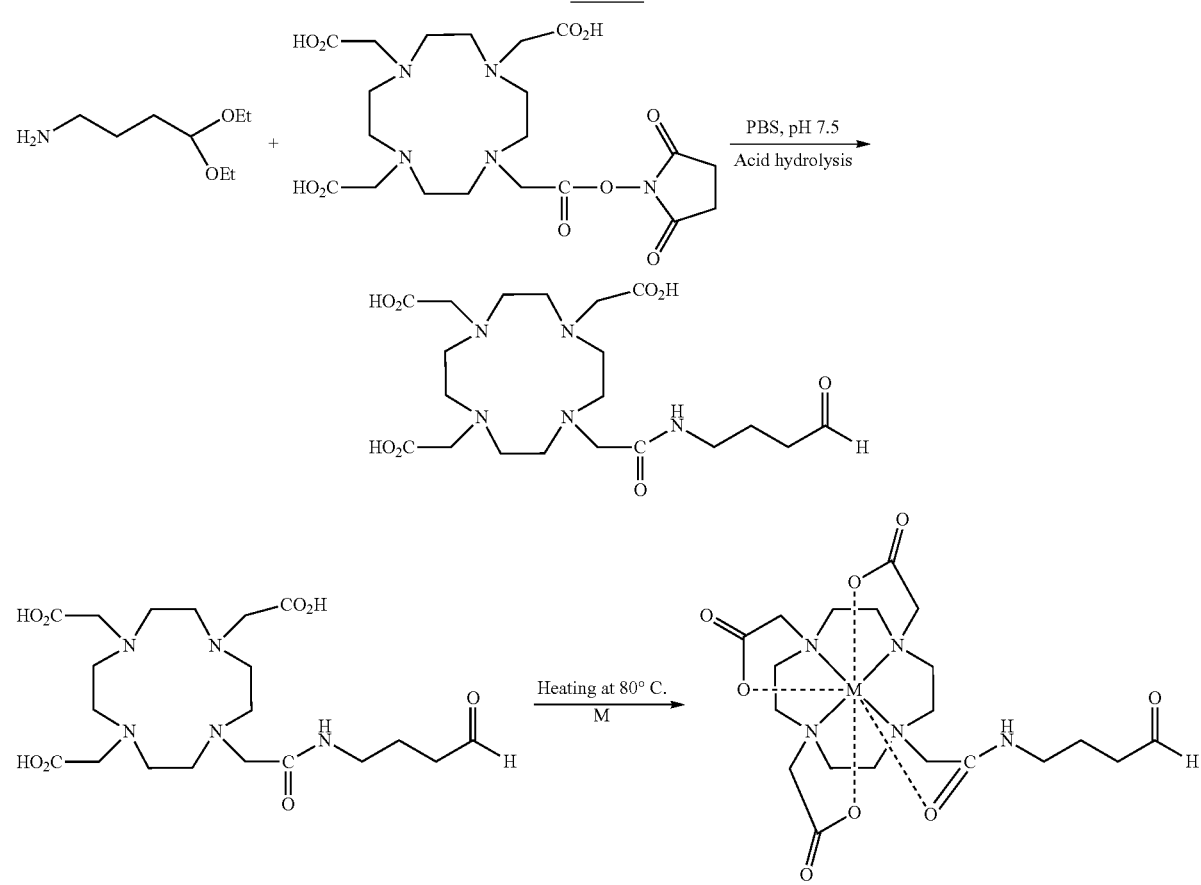

-continued
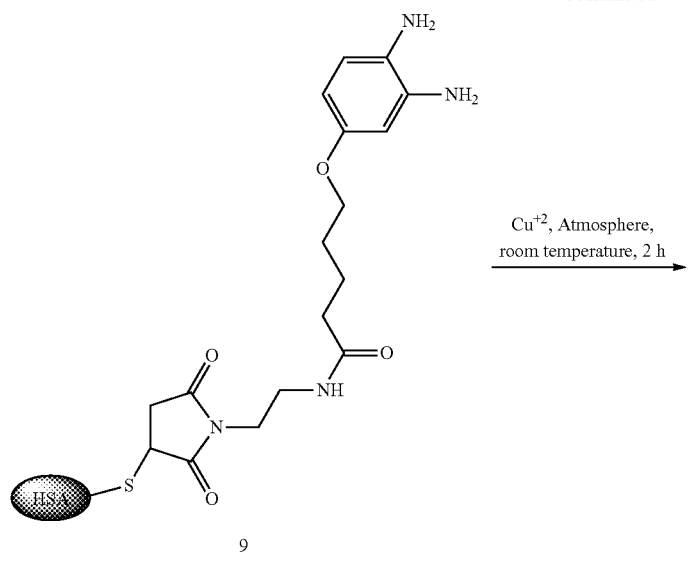
9
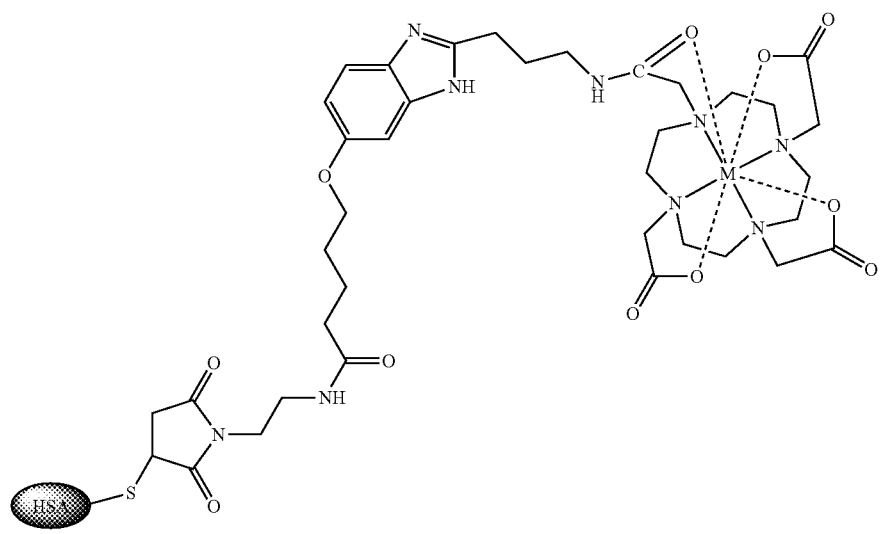
M = $^{89}$Zr
$^{111}$In
$^{68}$Ga

4. Evaluation of Biodistribution of [125I]-Labeled HSA in Animal

Figure 3:
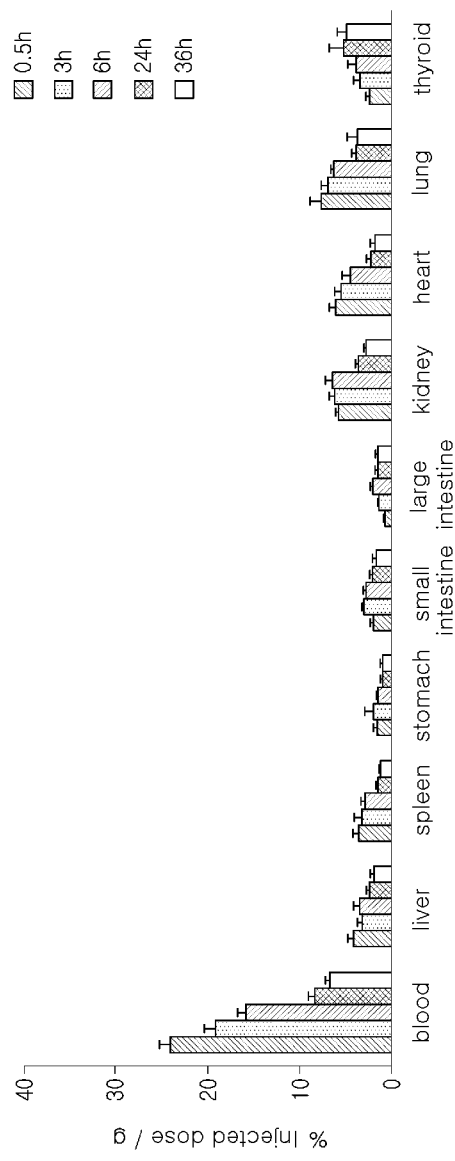
FIG. 3 shows evaluation results of in vivo biodistribution of normal ICR male mice (n=5) of [$^{125}$I] 9 compound.

In vivo organ distribution and in vivo behavior of the [125I]-labeled HSA ([125I] 9) of the present disclosure synthesized in the above 3.(1) were evaluated using ICR male mice. Each mouse was intravenously injected with 1 μCi of radiolabeled product, and the mice were sacrificed to collect in vivo distribution data at 0.5, 3, 6, 24 and 36 hours after injection. A large amount of radioactivity (24.07±1.28% ID/g) was found in the blood pool during the initial time points. The activity level was also significantly high even at 24 hours (8.32±0.72% ID/g) and 36 hours (6.73±0.48% ID/g) after injection (FIG. 3). This observation suggests that [125I] 9 has a long blood circulation time and may be used to increase the blood half-life of fast-eliminating drugs after conjugation with [125I] 9. Referring to FIG. 3, the uptake of radioactivity in other organs such as spleen, liver, small intestine, large intestine, lung, heart, stomach, and the like, was significantly high at an initial time point but decreased over time. A slightly higher kidney uptake suggests removal of the labeling compound via urine. Radioactivity accumulation in the thyroid usually represents in vivo deiodination, and was 5.20±1.61% ID/g and 4.86±1.01% ID/g at 24 hours and 36 hours post IV injection, respectively.

Meanwhile, biodistribution studies and data of direct radioiodinated HSA ([125I] 10) as shown in Scheme 8 showing the radioiodination reaction of the tyrosine ring of HSA, are summarized in Table 3 below.

Scheme 8

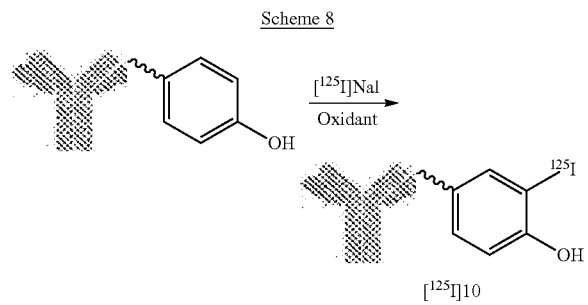

[125I]10

The radioactivity accumulation of [125I] 10 in the thyroid was normal at the first point but increased over time. Thyroid uptake was found to be 255.1±66.21% ID/g, and 395.2±59.98% ID/g at 24 hours and 36 hours post I.V injection, respectively. These results suggest high instability of radioactive iodine to the tyrosine ring in vivo. In addition, the structure of [125I] 5 was stable and was demonstrated to be completely different from iodotyrosine, which may undergo deiodination easily in vivo with the passage of time.

TABLE 3

In vivo biodistribution of [125I] 10

| Organ | Blood | Liver | Spleen | Stomach | Small intestine | Large intestine | Kidney | Heart | Lung | Thyroid |
|---|---|---|---|---|---|---|---|---|---|---|
| 0.5 h | 30.1 ± 1.28 | 5.1 ± 1.68 | 3.6 ± 2.32 | 1.6 ± 1.64 | 1.6 ± 0.86 | 0.88 ± 0.12 | 6.1 ± 0.28 | 5.9 ± 0.98 | 8.1 ± 2.31 | 2.1 ± 2.11 |
| 3 h | 25.3 ± 2.21 | 3.0 ± 2.03 | 3.2 ± 1.06 | 1.8 ± 0.98 | 2.2 ± 1.56 | 0.95 ± 0.17 | 5.3 ± 0.78 | 4.4 ± 1.32 | 7.7 ± 1.84 | 15.3 ± 5.61 |
| 6 h | 14.5 ± 6.01 | 2.8 ± 0.99 | 2.8 ± 1.55 | 5.8 ± 2.57 | 1.9 ± 1.22 | 1.1 ± 0.36 | 5.5 ± 0.31 | 3.5 ± 1.50 | 7.1 ± 0.98 | 75.3 ± 12.63 |
| 24 h | 8.3 ± 2.25 | 1.9 ± 1.68 | 1.6 ± 0.68 | 12.1 ± 2.21 | 1.7 ± 1.54 | 1.2 ± 0.54 | 4.2 ± 0.54 | 2.8 ± 0.87 | 5.2 ± 1.66 | 255.1 ± 66.21 |
| 36 h | 6.1 ± 3.25 | 1.8 ± 0.56 | 1.5 ± 1.02 | 14.2 ± 2.97 | 1.5 ± 0.91 | 1.0 ± 0.22 | 3.8 ± 0.66 | 2.1 ± 0.69 | 4.9 ± 1.59 | 395.2 ± 59.98 | n = 5 mice per group, and data represent % ID/g tissue.

The alkylaldehyde aryldiamine condensation reaction of the present disclosure has excellent radiochemical yield, and significantly excellent in-vivo stability of the result as compared to that of direct radioiodination to tyrosine using a severe oxidant such as chloramine-T. In the latter case, i.e., direct radioiodination, protein is damaged in radioisotope labeling, and the bioactivity of radiolabeled protein may be reduced. On the other hand, the alkylaldehyde aryldiamine condensation reaction of the present disclosure may be used for radioiodination of various small and large bioactive molecules based on the condensation reaction of aryl diamine with alkyl aldehyde.

Further, the radioisotope-labeled aldehyde compound of the present disclosure has significantly high in vitro and in vivo stability and does not respond to all functional groups of biologically active proteins.

Based on these results, it may be determined that the method for labeling a radioisotope of the present disclosure and the compound used therein have excellent characteristics that may be used for in-vivo targeting imaging.

As set forth above, the method for labeling a radioisotope according to the present disclosure and the related technology are based on a radioisotope labeling method using an aldehyde-diamine condensation reaction. Radioisotope-labeled biomolecules, fluorescent dyes or nanoparticle compounds, and the like, obtained by the present disclosure, are commercialized as a composition for medical diagnosis, and are likely to be commercialized for purposes of molecular imaging, diagnosis, treatment, and the like, and thus it is expected to contribute greatly to health promotion and welfare of the people.

While the present invention has been shown and described in connection with the embodiments, it will be apparent to those skilled in the art that modifications and variations can be made without departing from the spirit and scope of the invention as defined by the appended claims.

What is claimed is:

1. A method for labeling a radioisotope, comprising:

providing a diaminophenyl compound represented by Chemical Formula I below and including a biomolecule, a fluorescent dye or a nanoparticle bound thereto; and reacting the diaminophenyl compound and an aldehyde compound that is labeled with a radioisotope and represented by Chemical Formula II below at room temperature,

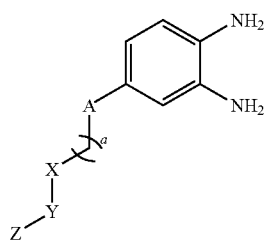

Chemical Formula I in Chemical Formula I,

A is $CH_2$ or O; a is 0 or an integer of 1 to 10; X is $CH_2$ or —CONH—; Y is $CH_2$ or

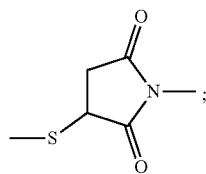

and Z is the biomolecule, the fluorescent dye or the nanoparticle,

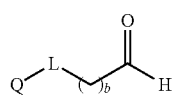

Chemical Formula II in Chemical Formula II, b is 0 or an integer of 1 to 10; and L is $CH_2$ or —CONH—; and Q is

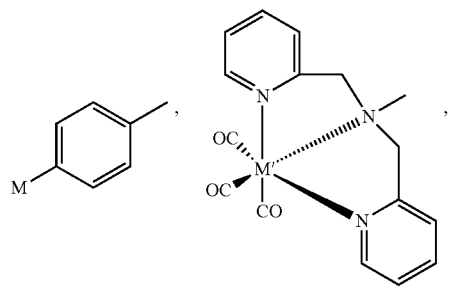

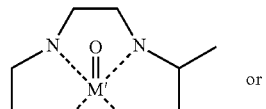

or

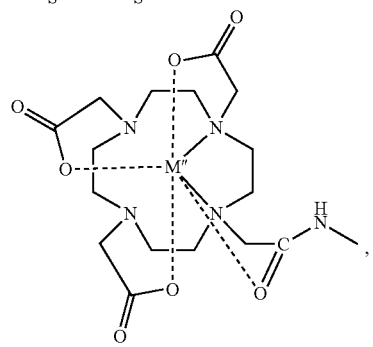

each of M, M' and M'' in Q is a radioisotope.

2. The method of claim 1, wherein the providing of a diaminophenyl compound includes:

providing a compound represented by Chemical Formula Ia below and including a thiol moiety; and reacting the compound represented by Chemical Formula Ia below and a compound represented by Chemical Formula Ib below to obtain the compound represented by Chemical Formula I, Z'—SH          Chemical Formula Ia in Chemical Formula Ia, Z' is the same as a structure except for a —SH moiety in Z when the biomolecule, fluorescent dye, or nanoparticle represented by Z in Chemical Formula I includes the thiol moiety; and Z' is the same as Z when the biomolecule, fluorescent dye or nanoparticle represented by Z does not include a thiol moiety,

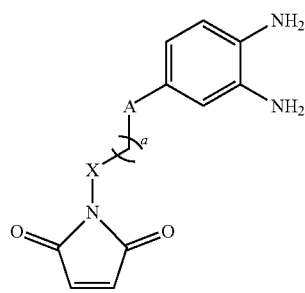

Chemical Formula Ib in Chemical Formula Ib, A, a and X are the same as defined in Chemical Formula I.

3. The method of claim 2, wherein the reacting of the compound represented by Chemical Formula Ia and the compound represented by Chemical Formula Ib is performed under a $Cu^{+2}$-based catalyst at room temperature and atmospheric pressure.

4. The method of claim 2, wherein the providing of a compound represented by Chemical Formula Ia and including a thiol moiety comprises providing a compound represented by Chemical Formula Ia by further substituting the thiol moiety into the biomolecule, the fluorescent dye or the nanoparticle Z' that does not include a thiol moiety.

5. The method of claim 1, wherein Z is the biomolecule and is at least one selected from the group consisting of a peptide, an antibody, and an oligonucleotide.

6. The method of claim 1, wherein Z is the nanoparticle and is at least one selected from the group consisting of a metal nanoparticle, a synthetic polymer nanoparticle, and a biopolymer nanoparticle.

7. The method of claim 6, wherein Z is the metal nanoparticle and is any one metal selected from the group consisting of gold (Au), platinum (Pt), palladium (Pd), silver (Ag), and copper (Cu); or any one metal oxide nanoparticle selected from the group consisting of cobalt (Co), manganese (Mn), iron (Fe), nickel (Ni), gadolinium (Gd), molybdenum (Mo), zinc (Zn), and chromium (Cr).

8. The method of claim 1, wherein Z is the fluorescent dye and is at least one selected from the group consisting of a cyanine dye, a fluorescein dye, and a rhodamine dye.

9. The method of claim 1, wherein the radioisotope is selected from the group consisting of I, F, Tc, Re, Ga, In, Zr, Y, Ho, Sm, and Lu.

10. The method of claim 9, wherein the radioisotope M is I or F, M' is Tc or Re, and M" is an element selected from the group consisting of Ga, In, Y and Zr.

11. A kit for labeling a radioisotope comprising:
a diaminophenyl compound represented by Chemical Formula I and including a biomolecule, a fluorescent dye or a nanoparticle compound bound thereto; and
a radioisotope-labeled aldehyde compound represented by Chemical Formula II,

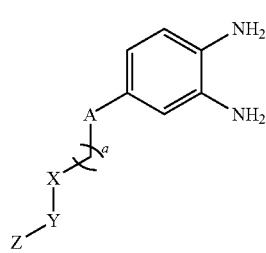

Chemical Formula I in Chemical Formula I,
A is $CH_2$ or O; a is 0 or an integer of 1 to 10; X is $CH_2$ or —CONH—; Y is $CH_2$ or

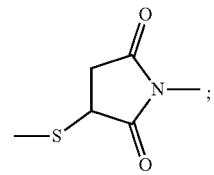

;

and Z is the biomolecule, the fluorescent dye or the nanoparticle compound,

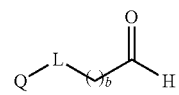

Chemical Formula II in Chemical Formula II, b is 0 or an integer of 1 to 10; and L is $CH_2$ or —CONH—; and
Q is

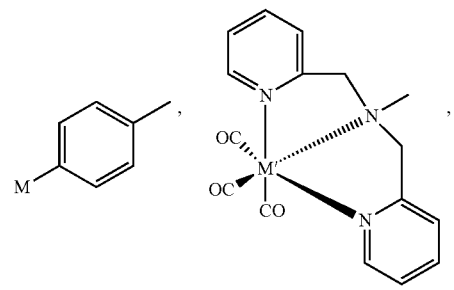

,

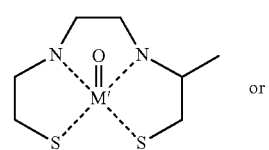 or

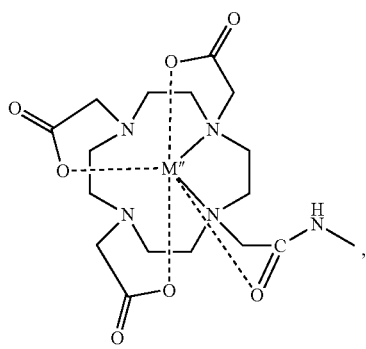

each of M, M' and M" in Q is a radioisotope.

12. The kit of claim 11, wherein the biomolecule is at least one selected from the group consisting of a peptide, an antibody, and an oligonucleotide; the nanoparticle compound is at least one selected from the group consisting of a metal nanoparticle compound, a synthetic polymer nanoparticle compound, and a biopolymer nanoparticle compound; the metal nanoparticle compound is any one metal selected from the group consisting of gold (Au), platinum (Pt), palladium (Pd), silver (Ag), and copper (Cu); or any one metal oxide selected from the group consisting of cobalt (Co), manganese (Mn), iron (Fe), nickel (Ni), gadolinium (Gd), molybdenum (Mo), zinc (Zn), and chromium (Cr); and the fluorescent dye is at least one selected from the group consisting of a cyanine dye, a fluorescein dye, and a rhodamine dye.

13. The kit of claim 11, wherein the radioisotope is selected from the group consisting of I, F, Tc, Re, Ga, In, Zr, Y, Ho, Sm, and Lu.

14. A radioisotope-labeled biomolecule, a radioisotope-labeled fluorescent dye or a radioisotope-labeled nanoparticle compound, represented by Chemical Formula IV below:

Chemical Formula IV

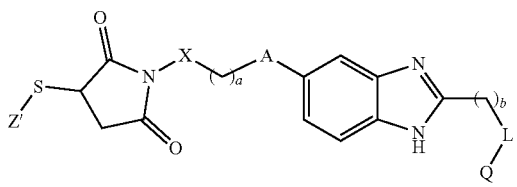

in Chemical Formula IV,

A is $CH_2$ or O; a is 0 or an integer of 1 to 10; X is $CH_2$ or —CONH—; Z' is a structure excluding a thiol group in a biomolecule, fluorescent dye or nanoparticle compound including the thiol group or substituted with the thiol group; b is 0 or an integer of 1 to 10; and L is $CH_2$ or —CONH—; and Q is

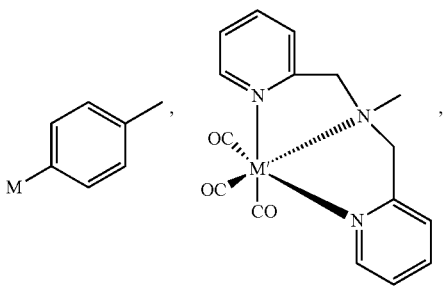

each of M, M' and M" in Q is a radioisotope.

15. A composition for medical diagnosis comprising:

a radioisotope-labeled biomolecule, a radioisotope-labeled fluorescent dye or a radioisotope-labeled nanoparticle compound represented by Chemical Formula IV below, as an active ingredient:

Chemical Formula IV

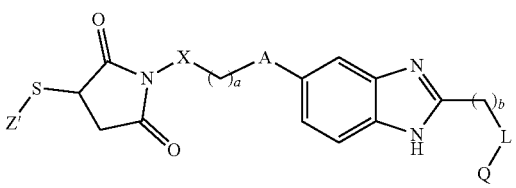

in Chemical Formula IV,

A is $CH_2$ or O; a is 0 or an integer of 1 to 10; X is $CH_2$ or —CONH—; Z' is a structure excluding a thiol group in a biomolecule, fluorescent dye or nanoparticle compound including the thiol group or substituted with the thiol group; b is 0 or an integer of 1 to 10; and L is $CH_2$ or —CONH—; and Q is
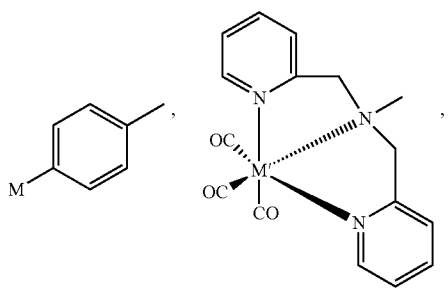, 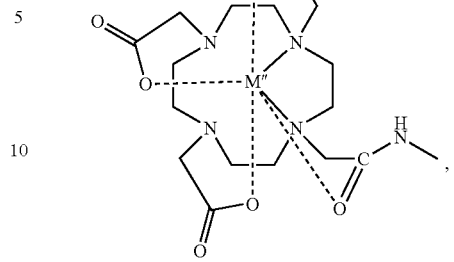,
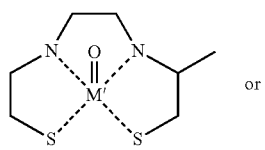 or
,
each of M, M' and M" in Q is a radioisotope.
16. The composition of claim 15, wherein the medical diagnosis is a diagnosis by single photon emission computed tomography (SPECT), positron emission tomography (PET), micro-PET, computed tomography (CT), magnetic resonance imaging (MRI) or target imaging of radiological diagnostic equipment.
* * * * *